United States Patent
Cross et al.

(10) Patent No.: US 9,538,943 B1
(45) Date of Patent: Jan. 10, 2017

(54) BLOOD GLUCOSE MONITOR AND METHOD OF USE THEREOF

(75) Inventors: William Howard Cross, Waco, GA (US); Frank Russell Denton, III, Lawrenceville, GA (US)

(73) Assignee: William Howard Cross, Waco, GA (US)

(*) Notice: Subject to any disclaimer, the term of this patent is extended or adjusted under 35 U.S.C. 154(b) by 133 days.

(21) Appl. No.: 13/317,863

(22) Filed: Oct. 31, 2011

Related U.S. Application Data

(60) Provisional application No. 61/456,022, filed on Oct. 29, 2010.

(51) Int. Cl.
| | |
|---|---|
| *A61B 5/1455* | (2006.01) |
| *A61B 5/145* | (2006.01) |
| *A61B 5/157* | (2006.01) |
| *G01N 27/327* | (2006.01) |
| *A61B 5/00* | (2006.01) |

(52) U.S. Cl.
CPC .......... *A61B 5/14532* (2013.01); *A61B 5/157* (2013.01); *A61B 5/4839* (2013.01); *G01N 27/3271* (2013.01)

(58) Field of Classification Search
USPC .................................................. 600/309–344
See application file for complete search history.

(56) References Cited

U.S. PATENT DOCUMENTS

| | | | | |
|---|---|---|---|---|
| 5,507,288 | A * | 4/1996 | Bocker et al. | 600/322 |
| 6,641,533 | B2 * | 11/2003 | Causey et al. | 600/300 |
| 8,571,618 | B1 * | 10/2013 | Lamego et al. | 600/316 |
| 2005/0043598 | A1 * | 2/2005 | Goode et al. | 600/316 |
| 2005/0192492 | A1 * | 9/2005 | Cho et al. | 600/316 |
| 2009/0036760 | A1 * | 2/2009 | Hayter | 600/316 |
| 2010/0221762 | A1 * | 9/2010 | Sterling et al. | 435/12 |

* cited by examiner

*Primary Examiner* — Tse Chen
*Assistant Examiner* — Marjan Fardanesh
(74) *Attorney, Agent, or Firm* — Denton Intellectual Property Law Firm, LLC; F. Russell Denton

(57) ABSTRACT

The invention is an improved blood glucose monitor and method of use thereof, comprising the combination of a noninvasive blood glucose detector with a blood sample reader for invasively obtained samples and a monitor for tracking blood glucose concentrations over time. The invention enables real time calibration of noninvasive blood glucose detection for continuous monitoring.

15 Claims, 1 Drawing Sheet

Caricature of one embodiment according to the invention.

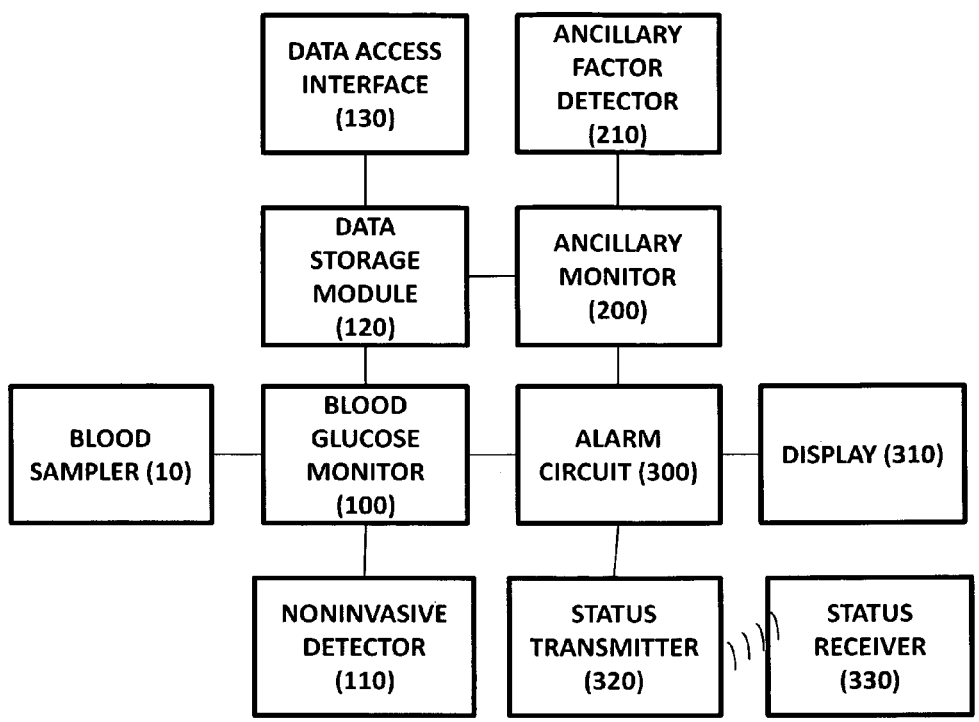
Caricature of one embodiment according to the invention.

BLOOD GLUCOSE MONITOR AND METHOD OF USE THEREOF

PRIORITY APPLICATIONS

This application claims priority to a provisional patent application U.S. Ser. No. 61/456,022, filed Oct. 29, 2010 by the same inventors with the same title.

FIELD OF THE INVENTION

The preferred embodiment relates generally to a blood glucose monitor and method of use thereof, and more specifically to a glucose monitor comprising a blood sampler in combination with a noninvasive glucose detector.

BACKGROUND OF THE INVENTION

Diabetes mellitus is a carbohydrate metabolism disorder caused by insufficient insulin production and or reduced sensitivity to insulin. Consequently the cells are inhibited from normal glucose utilization, resulting in abnormally high blood sugar levels and a variety of maladies. Chronic complications include diabetic retinopathy (retinal changes leading to blindness), kidney disease and frequent infection. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes.

Although complications can often be avoided by careful management of blood glucose levels, complete control is elusive. For instance, "hypoglycemia unaware" diabetic persons who comply with medical protocols for insulin administration may nevertheless have hypoglycemic episodes and be completely unaware that diabetic shock is setting in until after the symptoms have manifested. This puts them at risk during sleep, sports, driving, and other daily activities, prevents bystanders from calling for timely medical intervention, and lack of coordination makes the hypoglycemic individual appear to be under the influence of drugs or alcohol. Consequently diabetic drivers in particular are at risk for arrest without culpability, and diabetic drivers of commercial motor vehicles often face bans abroad and onerous compliance requirements under the U.S. federal exemption program.

Blood glucose management has traditionally relied on sampling the blood; clinically the sample may be obtained by trained personnel; in non-clinical settings the diabetic individual often draws blood for a test strip by painfully pricking a finger with a lancet. The test strip is then inserted into an electronic glucose measuring device, which determines glucose levels based on electrochemistry or the degree of color change from a chemical reaction on the test strip and displays the results on the measuring device. Although the test strips are still the most reliable glucose detection method and are widely used, they are an imperfect solution. The strip method provides data only at the test times, and results may have a time lag relative to real changes in body glucose because they measure the glucose in interstitial fluid of the blood and not in the blood cells themselves. Also, because sampling is usually several hours apart the blood glucose levels can and often do change substantially for the worse without the individual being aware of it. In order to obtain continuous data, other invasive methods have been introduced employing implanted detection hardware. Common drawbacks of the invasive monitors include discomfort, complexity, potential for infection, formation of scar tissue that seals off the portal for sampling blood, and typical time lags of 20 minutes before data is reported by the device.

In recent decades over 100 major projects have been undertaken to develop reliable non-invasive blood glucose detection. However for the most part those projects have met with failure, on a spectacular scale in many cases. Those technologies and success criteria for such projects are described at length in *The Pursuit of Noninvasive Glucose: "Hunting the Deceitful Turkey* (John L. Smith, 2006), posted at www.mendosa.com/noninvasive_glucose.pdf. Among the techniques used have been infrared (IR) and near-infrared (NIR) spectroscopy, thermal infrared spectroscopy (TIR), Raman spectroscopy, nuclear magnetic resonance (NMR), electron spin resonance (ESR), impedance spectroscopy, dielectric spectroscopy, magneto-wave (i.e., photoacoustic) spectroscopy, and reverse iontophoresis. In the recent decade Esenaliev and Prough developed indirect but highly accurate glucose detection methods based on the use of optical coherence tomography (OCT) or ultrasound, whereby changes in tissue thickness were found to have an inverse correlation to blood glucose levels; thus they monitored tissue thickness by means of time-of flight for pulse signal echoes and found this tracked glucose levels with high fidelity relative to values obtained by test strips, the gold standard. See, for instance, U.S. Patent Publication No. 2007/0255141 by Esenaliev and Prough.

Nevertheless a variety of concerns continue to plague noninvasive technologies, as reported in Smith's book cited above. Perhaps the most important problem is that although the noninvasive methods are often excellent at correlating with known glucose levels, they are poor at predicting the exact concentrations in control experiments where the researcher is not told the absolute value of the benchmark glucose levels in a concentration plot over time. I.e., the correlation is not tracking with causation. Consequently the amount of uncertainty often exceeds the FDA's permissible limit of +20 mg/dl for accuracy in determining glucose concentration; this is quite substantial when compared to the normal range of 80 to 120 mg/dl. The results are also subject to variation caused by differences in room temperature or humidity. See, e.g., Smith at pp. 56-69.

Thus there is an ongoing and urgent need for improved non-invasive blood glucose monitors.

SUMMARY OF THE INVENTION

The invention is an improved blood glucose monitor and method of use thereof. The invention combines the best of non-invasive detection features (including continuous or near-continuous monitoring) with the best of invasive detection features (high accuracy).

In particular, the invention employs an integrated blood glucose monitoring device comprising a blood sampler, a noninvasive detector and a blood glucose monitor. The device optionally further comprises a data storage module and a data access interface, enabling tracking and data analysis for blood glucose trends over time. In certain embodiments the device further comprises an alarm circuit for indicating when a subject is near to or outside the safe and healthy glucose levels. The subject's data and or data trends are shown on a display, and an optional transmitter and optional receiver enable communication with third parties such as family when a health need arises. Devices according to the invention optionally further comprise an ancillary factor detector and ancillary monitor for tracking other physiological parameters such as heart rate, body temperature, blood pressure, and for tracking environmental conditions.

The invention includes methods of using the device, including calibration of the non-invasive detection by the invasively obtained samples, monitoring blood glucose concentration and rates of change in it, and displaying those values and reporting them remotely. The methods are suitable for use with humans, pets, livestock, research animals and display animals, and can be used with any of a wide variety of noninvasive detection modes.

BRIEF DESCRIPTION OF THE FIGURES

FIG. 1 is a caricature of one embodiment according to the invention.

DESCRIPTION OF THE INVENTION

The present invention is an improved blood glucose monitor and method of use thereof, comprising the use of a test strip reader with a continuous noninvasive blood glucose monitor. The following observations led to development of the invention.

First, the historic and ongoing difficulty of obtaining good correlation but poor predictive power for most glucose detection methods suggested that they would benefit from recalibration every few hours by a blood sample to ensure safety. This overcomes the problem of drift in the user's extent of hydration, electrolyte levels, external temperature and humidity, ethical drug use and so forth. This belt-and-suspenders approach of using regular blood sampling to regularly re-calibrate a noninvasive monitor offers continuous data without requiring either the detection mode or the corresponding algorithm to be perfectly exact, and also reduces the discomfort and likelihood of infection, scarring and instrument error that hobble continuous invasive monitoring.

But it is not only the non-invasive monitor that needs compensating measures: even the highly reliable test strips are problematic because they provide only single values isolated at different points in time. In many cases the exact concentration of blood glucose at a single instant in time is not as informative as the general trend in the blood glucose levels over the prior hour: has the blood sugar level been stable or has it been falling (or rising) rapidly? Particularly rapid changes even while still in the normal range justify earlier intervention than one would undertake otherwise, particularly when the trend is toward hypoglycemia.

To our knowledge all prior noninvasive technologies have attempted to replace the test strips and strip readers altogether for the end user, whereas we find there is a great and immediate benefit in combining blood sampling with noninvasive detectors. In a particular embodiment, devices according to the invention comprise a noninvasive detection module and a blood sample testing module. In a particular embodiment the sample tester is a test strip reader but the invention is not limited to test strips or readers. In certain preferred embodiments electronic output from one or more assays at the strip reader is read by a module that uses the data to calibrate the noninvasive detection module.

The description of the invention will be better understood by consideration of the following definitions for the terms as used herein.

The term subject refers to human subject, a non-human mammalian subject or another type of subject, wherein the subject's blood glucose concentration is being measured or is to be measured. The term subject includes but is not limited to: pets such as dogs, cats, rodents, birds, reptiles, amphibians, fish and other pets; livestock such as cattle, horses, sheep, goats, alpaca, chickens, geese, pigs, and other livestock; research animals such as mice, rats, pigeons, dogs, cats, captive woodland creatures, captive aquatic creatures, captive birds, captive desert creatures, captive marsh creatures and other research animals; and display animals such as zoo animals, carnival display animals, commercial aquarium animals, and other display animals.

The term blood glucose refers to molecular glucose that exists in its monomeric state, having no covalent bonds to any other molecule. The term is not limited by whether glucose is in its cyclic or acyclic form. The term blood glucose as used herein includes interstitial blood glucose, and where the context and detection methodology can measure it also includes intracellular blood glucose.

The term detector as used with respect to blood glucose levels means a device that correlates data from blood or other tissues with relative levels of blood glucose.

The term noninvasive means probing of physiological functions in a subject without puncturing or otherwise penetrating the skin or entering a body cavity. Thus for example using any instrumentality to draw blood is invasive, even if the instrumentality operates by force (such as compelling blood expression through application of a vacuum).

The term blood glucose monitor means a circuit for detecting, recording, comparing and or transmitting signals from a noninvasive detector and optionally from a blood sampler. Suitable circuits for monitors are familiar to persons of ordinary skill in the art. In one embodiment the inputs from a blood sampler serve as a benchmark to calibrate the values from a noninvasive detector.

The term noninvasive detector means a detector that performs its function without requiring blood samples or contact with blood or input data that is otherwise obtained by invasive methods. Noninvasive detectors include among others those that transmit into and receive back from the body electromagnetic waves at energy levels below levels that would compromise the integrity of tissues. Nonlimiting illustrative examples include ultrasound devices and optical coherence tomography devices that determine tissue thickness. Other nonlimiting illustrative examples include detector that employs other electromagnetic waves, radiofrequency waves, impedance spectroscopy, dielectric spectroscopy, magneto-wave spectroscopy such as photoacoustic technology, beam-splitting optics, reverse iontophoresis, or other signals such as are disclosed in U.S. Pat. Pub. Nos. 2009/0156915 by Cross or 2007/0255141 by Esenaliev and Prough, the contents of both of which are incorporated herein by reference. Additional nonlimiting illustrative examples include devices that determine blood glucose concentration by means of infrared light, near-infrared light, thermal infrared spectroscopy, Raman spectroscopy, polarized light, other optical media, nuclear magnetic resonance, and electron spin resonance (also known as electron paramagnetic resonance).

The term blood sampler means any analytical device that is capable of determining glucose levels in blood from a blood sample. An illustrative blood sampler is a test strip reader as is commonly used for detecting glucose levels in the blood of diabetic subjects as placed onto a chemical or electrochemical test strip for detection, but the term blood samplers as used herein refers to any analytical device capable of determining glucose concentrations of blood in vitro.

The term integrated blood glucose monitoring device as used herein means a device that comprises a blood sampler, a noninvasive detector and a blood glucose monitor.

The term data storage module means a device in which data may be stored and from which it may be retrieved. A nonlimiting illustrative data storage device is a computer memory chip. Suitable memory chips and memory circuits are familiar to persons of ordinary skill in the art. The term data storage module as used herein is not limited by the type or scope of data stored therein, and data storage modules in devices according to the invention may optionally include a chronological log for detected glucose levels, calibration benchmarks for glucose concentration, and values that reflect the offset of noninvasively detected values from those determined by a blood sampler.

The term data access interface means a portal for the transfer of information to and from devices. Nonlimiting illustrative examples include USB ports, electronic busses, infrared ports and other data transfer interface for downloading data from a device, and or optionally for uploading software upgrades or new operating parameters.

The term alarm circuit means an electronic circuit having a function of issuing an alarm when detection data for a physiological function falls outside a programmed boundary for health and safety. Such circuits are familiar to persons of ordinary skill in the art, and may optionally include parameters and algorithms identifying blood glucose concentration thresholds or blood glucose rate change thresholds that warrant and alarm or other notice for further review or medical intervention.

The term display means a display of electronically managed data such as an LED display, LCD display or other display known to persons of ordinary skill in the art. For devices according the invention, the display may show data on blood glucose levels and optionally blood glucose concentration rates of change, and may optionally show ancillary factors such as time, hydration, sodium concentration, potassium concentration, temperature, pressure, heart rate, blood pressure, concentration of ethical drugs or other drugs in the blood, detector signal-to-noise ratio, detector signal drift or other factors.

The term ancillary factor detector means a detector that determines (1) one or more value for a non-physiological condition; or (2) one or more values for a physiological condition other than the concentration of glucose in the blood or the rate of change for blood glucose concentrations. Nonlimiting illustrative physiological conditions detected by ancillary factor detectors optionally include duration of time for detection, sufficiency of hydration in a subject, blood sodium concentration, blood potassium concentration, body temperature, blood pressure, heart rate, external pressure on skin, concentration of one or more drugs in the blood, diagnostic characteristics of fluids in the lymph and other body fluids, and other physiological conditions. Nonlimiting illustrative non-physiological conditions determined by a ancillary factor detector optionally include time of day, passage of time, ambient external temperature, atmospheric pressure, atmospheric humidity, electronic signal-to-noise ratio, electronic signal drift of detectors, and other conditions.

The term ancillary monitor means a circuit for detecting, recording, comparing and or transmitting signals from a noninvasive ancillary factor detector and optionally from a blood sampler, wherein the signals either: (1) convey a value for a non-physiological condition; or (2) are diagnostic for a physiological condition other than the concentration of glucose in the blood or the rate of change for blood glucose concentrations. Suitable circuits for ancillary monitors are familiar to persons of ordinary skill in the art.

The terms concentration and rate of change respectively mean the concentration and its rate of change for glucose in a subject's blood.

The term time of flight means the time required for a transmitted signal from the electromagnetic spectrum to penetrate and echo back through the tissue(s) of interest in a subject.

The term status transmitter means a transmitter of electronic signals, and may be an electrical cord, telephone line, radiofrequency communications transmitter, infrared communications transmitter, or another communications transmitter such as is familiar to persons of ordinary skill in the art. In some embodiments the transmitter transmits an audible signal. In a particular embodiment the transmitter is a Bluetooth transmitter. In various embodiments the transmission communications mode may be selected or altered at the discretion of the user or the user's family. In some embodiments the transmission mode employs remote signals that do not require a transmission line and is selected from the group consisting of infrared signals, visual optical signals, radiofrequency (rf) signals, electromagnetic signals, sound signals, vibratory signals, and mechanical signals.

The term status receiver means a device for receiving communications of electronic signals and optionally corresponds to the communication medium of the status transmitter. The status receiver may be an electrical cord, telephone line, radiofrequency communications receiver, infrared communications receiver, or another communications receiver such as is familiar to persons of ordinary skill in the art. In some embodiments the receiver receives an audible signal. In a particular embodiment the receiver is a Bluetooth receiver. In various embodiments the receiver communications mode may be selected or altered at the discretion of the user or the user's family. In some embodiments the reception mode detects remote signals that do not require a transmission line and is selected from the group consisting of infrared signals, visual optical signals, radiofrequency (rf) signals, electromagnetic signals, sound signals, vibratory signals, and mechanical signals.

FIG. 1 illustrates one nonexclusive embodiment of the invention. In this embodiment a blood glucose monitor (100) is in electrical or other communication with a noninvasive detector (110), a blood sampler (10), a data storage module (120), and an alarm circuit (300). Data storage module (120) is further in electrical or other communication with a data access interface (130). Alarm circuit (300) is further in electrical or other communication with an ancillary monitor (200), a display (130), and a status transmitter (320). The ancillary monitor is further in electrical or other communication with both data storage module (120) and an ancillary factor detector (210). Status transmitter (320) is further in communication with a status receiver (330). Examples of being in non-electrical communication include communications transmissions by means of infrared signals, visual optical signals, radiofrequency signals, electromagnetic signals, sound signals, vibratory signals, mechanical signals and the like.

Referring again to FIG. 1, blood sampler (10) is optionally a test strip reader but may be any analytical device capable of determining glucose levels in blood.

Referring again to FIG. 1, noninvasive detector (110) is optionally a detector that employs ultrasound or optical coherence tomography to determine tissue thickness but may alternatively be a detector that employs other electromagnetic waves, radiofrequency waves, impedance spectroscopy, dielectric spectroscopy, magneto-wave spectroscopy such as photoacoustic technology, beam-splitting optics, reverse iontophoresis, or other signals such as are disclosed in U.S. Pat. Pub. Nos. 2009/0156915 by Cross or 2007/0255141 by Esenaliev and Prough, the contents of both of which are incorporated herein by reference.

Referring again to FIG. 1, blood glucose monitor (100) is a circuit for detecting, recording, comparing and or transmitting signals from the blood sampler (10) and noninvasive detector (110). Suitable circuits for monitors are familiar to persons of ordinary skill in the art. In this embodiment the inputs from the blood sampler (10) serve as a benchmark to calibrate the values from the noninvasive detector (110).

Referring again to FIG. 1, data storage module (120) is a memory circuit such as is familiar to persons of ordinary skill in the art, and may optionally include a chronological log for detected glucose levels, calibration benchmarks, and shift values from the noninvasive detector (110). The data access interface (130) may be a USB port or other data transfer interface for downloading data from the device, and or optionally for uploading software upgrades or new operating parameters.

Referring again to FIG. 1, ancillary monitor (200) is optional, and is a monitor such as is familiar to persons of ordinary skill in the art. Where an ancillary monitor (200) is present, the ancillary analyte detector (210) is a detector such as is familiar to persons of ordinary skill in the art, and may optionally be selected from concentration detectors for additional analytes such as water, sodium ions, potassium ions, or ethical drugs, or may be selected from detectors for factors such as temperature, atmospheric or other topical pressure, blood pressure, heart rate, signal-to-noise ratio, signal drift or other relevant factors.

Referring again to FIG. 1, alarm circuit (300) is a circuit such as is familiar to persons of ordinary skill in the art, and may optionally include parameters and algorithms identifying threshold glucose levels or threshold glucose change rates warranting further review or medical intervention. Display (310) is a display such as is familiar to persons of ordinary skill in the art, such as an LED display, LCD display or other display, wherein data on blood glucose levels, change rates, and ancillary factors such as time, hydration, sodium concentration, potassium concentration, temperature, pressure, heart rate, blood pressure, ethical drug concentration, signal-to-noise ratio, signal drift or other factors may optionally be displayed.

Referring again to FIG. 1, status transmitter (320) is an optional transmitter such as is familiar to persons of ordinary skill in the art, and may optionally include be an electrical cord, radiofrequency communications transmitter, infrared communications transmitter, or other communications transmitter. When transmitter (320) is present, status receiver (330) is optionally present, and is a receiver such as is familiar to persons of ordinary skill in the art, and may correspond to the communication media of the transmitter. In one embodiment the transmitter transmits a digital or analog electrical signal. In another embodiment the transmitter transmits a radiofrequency signal. In a further embodiment the transmitter transmits an infrared signal. In an additional embodiment the transmitter transmits an audible signal. In a particular embodiment the transmitter is a Bluetooth transmitter. In some embodiments the device according to the invention is used during a diabetic individual's sleep, the transmitter has a radiofrequency signal, and the receiver is telephonic to alert the individual's other family members at locations remote from the individual's sleeping quarters. In various embodiments the transmission communications mode may be selected or altered at the discretion of the user or the user's family. The transmissions can be performed along phone lines, dedicated health information cables, hard-wired Internet, wirelessly over the Internet, cable channels, audible signals, or other communication media.

In some embodiments devices according to the invention are in a wristwatch format; in others they are in a box format; in others they are in a hat format; in others there are in a chest strap format; in still others they are in a bandage format. In particular embodiments the device rests on a sound-propagating pad such as a gel pad for ultrasound. In various embodiments the device is located on the wrist, ankle, chest, extremity, forehead, ear, or other part of the body.

In particular embodiments devices according to the invention have a watch mode—i.e., show the time. In some embodiment the invention has straps that can be readily replaced with others having a different esthetically appealing design to suit the wearer's fashion tastes.

In some embodiments the invention is used during sleep. In other embodiments the invention is used while driving. In other embodiments the invention is used during sports. In some embodiments the invention is used during emergency care for the individual.

Further illustrative embodiments include the following.

EXAMPLE 1

A device having a housing, containing:
an rf transmitter disposed in the housing and configured and arranged to transmit data relating to (a) analyte signals from at least one sensor, or (b) changes in at least one dimension of at least one tissue or tissue layer or absolute or relative changes in time of flight of ultrasound or optical pulses;
an analyte sensor port coupled with the housing and configured to receive data from an in vitro analyte sensor, wherein the analyte sensor generates an analyte signal from a fluid sample; and
a processor disposed in the housing and configured to validate the data relating to analyte signals from the non-invasive analyte sensor based at least in part on the analyte signal from the in vitro analyte sensor.

The analyte of this example is blood glucose. When a blood sample is placed on a blood glucose test strip and the test strip is placed into a test strip reader in the invention device, the reader generates digital data quantifying the concentration of glucose in the sample. In particular embodiments the reader then sends that data to a comparator that evaluates how closely the blood glucose concentration determined non-invasively correlates with the determination in vitro. In certain embodiments the non-invasive sensor employs ultrasound signals or optical coherence tomography. In other embodiments the non-invasive sensor employs infrared light, near-infrared light, Raman spectroscopy, polarized light, or another optical means for the non-invasive detection of glucose. In still other embodiments the non-invasive sensor employs electromagnetic waves, radiofrequency waves, impedance spectroscopy, dielectric spectroscopy, magneto-wave spectroscopy such as photoacoustic technology, beam-splitting optics, reverse iontophoresis, or other signals such as are disclosed in U.S. Pat. Pub. Nos. 2009/0156915 by Cross or 2007/0255141 by Esenaliev and Prough.

EXAMPLE 2

The device according to Example 1, further comprising a USB port for connection to a computer or other electronic device, allowing for the transfer of data.

EXAMPLE 3

A device according to Example 1, further comprising an in vitro analyte sensor positioned with an analyte sensor port.

EXAMPLE 4

A device according to Example 1, further comprising a processor configured to execute a first predetermined routine (switch to calibration mode and switch the display to read an in vitro analyte sensor in the sensor port) when it detects the in vitro analyte sensor in the sensor port.

EXAMPLE 5

A device according to Example 5 further comprising a memory configured to store data from an in vitro analyte sensor as a calibration parameter.

EXAMPLE 6

A device according to Example 4, wherein the processor is configured to recognize a calibration parameter based upon a position of insertion of an in vitro analyte sensor (test strip).

EXAMPLE 7

A device according to Example 4, wherein the processor is configured to recognize a calibration parameter based on an electrical characteristic of insertion of an in vitro analyte sensor (test strip).

EXAMPLE 8

A device according to Example 4, wherein the processor is configured to recognize a calibration parameter based on an electrical resistance to the insertion of an in vitro analyte sensor (test strip).

EXAMPLE 9

A device according to Example 4, wherein the analyte sensor port comprises a first contact structure and a second contact structure configured to contact the insertion of the in vitro analyte sensor (test strip).

EXAMPLE 10

A method for noninvasive glucose sensing including the steps of: measuring a thickness of a target tissue and determining a glucose value from the thickness of the target tissue in accordance with a target tissue thickness measured against the calibration parameter of Example 5.

EXAMPLE 11

A method for noninvasive glucose sensing including the steps of: measuring a time of flight of ultrasound or optical pulses in a target tissue and determining a glucose value from the time of flight in the target tissue in accordance with a time of flight versus the calibration parameter of Example 5.

EXAMPLE 12

A method for continuous noninvasive glucose sensing including the steps of: measuring a time of flight of ultrasound or optical pulses in a target tissue and determining a glucose value from the time of flight in the target tissue in accordance with a time of flight versus the calibration parameter of Example 5, and displaying a blood glucose concentration value from the device.

EXAMPLE 13

A method for monitoring glucose levels comprising logging the physiological parameter in Example 5, by repeated measurements and predicting the evolution of the glucose levels of Example 12, wherein the evolution of the glucose levels over an interval of autonomous evolution is predictable by a parametric model. The interval of autonomous evolution is defined in this Example and hereafter as falling within a period of time between two successive calibrations of the device wherein the evolution represents a relatively linear trend line for blood glucose levels.

EXAMPLE 14

A method for prediction comprising the steps of adding the glucose measurements of Example 5, to the glucose levels in Example 12, and to the previous measurements of the interval of autonomous evolution. The method includes conducting a test to determine whether the new measurement together with the previous measurements still form an interval of autonomous evolution and, depending upon this test, adapting the interval of autonomous evolution and/or adapting the parametric model and predicting the evolution of the glucose levels, using the parametric model for the adapted interval of autonomous evolution.

EXAMPLE 15

The method according to Example 14, wherein the test is conducted for whether the new measurement together with the measurements of the adapted interval form an interval of autonomous evolution.

EXAMPLE 16

The method according to Example 14, wherein the steps of removing at least one measurement and conducting the test is repeated until the adapted interval is an interval of autonomous evolution.

EXAMPLE 17

The method according to Example 14, wherein the step of conducting the test comprises calculation of the error by comparing glucose levels of the new measurement(s) to a predicted glucose level of a preceding iteration, or determination of a new set of parameters for the parametric model, wherein the parametric model with the new set of parameters optimally describes the evolution of the glucose level over the interval of autonomous evolution including the new measurement and calculation of a distance between a new vector, defined by the new set of parameters and a former vector, defined by a set of parameters of a preceding iteration.

EXAMPLE 18

The method according to Example 14, further comprising the step of alarming a patient when the predicted evolution of the glucose level is below or above a dangerous threshold.

EXAMPLE 19

The method according to Example 14, further associating a likelihood value to the predicted evolution of the glucose level, the prediction of the evolution of the glucose level being discarded if the likelihood value is below a certain threshold value.

EXAMPLE 20

The method according to Example 14, further wherein the step of predicting the evolution of the glucose level is conducted using a multitude of parametric models for the adapted interval of autonomous evolution and obtaining the prediction as a weighted sum of the predictions of the multitude of parametric models, wherein the weights of the parametric models are defined adaptively, preferably depending upon a quality of the prediction of each parametric model in the previous iterations and/or depending upon the number of iterations each parametric model has been used.

EXAMPLE 21

The method according to Example 14, wherein each parametric model is discarded when its weight drops below a threshold value and a substitute parametric model is added to the multitude of parametric models or upon calibration according to Example 5.

EXAMPLE 22

The method according to Example 20, wherein a threshold value is adopted or modified, particularly the threshold value for the weight of the parametric models and or the threshold for the likelihood value.

EXAMPLE 23

The method according to Example 1, for monitoring the glucose level of a user, comprising a means for measuring the glucose level of a user as in Example 13, and a computing means, the computing means having a data storage for storing measurements and a processor unit for calculating a prediction of the evolution of the glucose level, according to the method of Example 1.

EXAMPLE 24

The method according to Example 13, further comprising an output means for outputting alarm messages to the user.

EXAMPLE 25

The method according to Example 14, further comprising the step of displaying to a user on the integrated monitor, a first output of sensor data displayed simultaneously with an analyte concentration target range, a second output of said sensor data versus the calibration parameter of Example 5, and displaying the glucose value on integrated monitor and display unit of Example 1, and a third output of a directional arrow indicative of both an amplitude and a direction of a rate of change of analyte concentration associated with sensor data for the time period.

EXAMPLE 26

The method according to Example 25, wherein the directional arrow has a rotational direction with at least about 45 degrees of resolution.

EXAMPLE 27

The method according to Example 25, wherein the directional arrow has a rotational direction with at least about 180 degrees of resolution.

EXAMPLE 28

The method according to Example 25, wherein displaying the first output comprises displaying one or more clinical risk zones.

EXAMPLE 29

The method according to Example 25, wherein the target range is defined by a colored region.

EXAMPLE 30

The method according to Example 25, wherein the target range is represented by an upper boundary and a lower boundary.

EXAMPLE 31

The method according to Example 25, wherein an upper boundary and a lower boundary are user configurable.

EXAMPLE 32

The method according to Example 25, wherein displaying comprises displaying at least one of a predicted analyte value or a range of predicted analyte values.

EXAMPLE 33

The method according to Example 25, wherein sensor data comprises calibrated sensor data.

EXAMPLE 34

The method according to Example 25, further comprising calibrating sensor data to obtain calibrated sensor data, wherein the rate of change is associated with calibrated sensor data.

EXAMPLE 35

The method according to Example 34, further comprising updating calibration or recalibrating sensor data associated with a change in sensitivity.

EXAMPLE 36

The method according to Example 34, wherein calibrating sensor data comprises compensating for a time lag between the analyte concentration measured by the sensor data from analyte signals from the at least one sensor and the in vitro analyte sensor (test strip).

EXAMPLE 37

The method according to Example 36, wherein compensating comprises matching an analyte concentration measurement by the sensor data from analyte signals from the at least one sensor with sensor data obtained from about 5 minutes to about 20 minutes after the analyte concentration measurement by the in vitro analyte sensor (test strip).

EXAMPLE 38

The method according to Example 25, wherein the first output and the second output are simultaneously displayed.

EXAMPLE 39

The method according to Example 1, for the glucose level of a user, comprising a physiological parameter measuring means and a computing means, the computing means having a data storage for storing the measurements and a processor unit for calculating a prediction of the evolution of the glucose levels, and transmitting the glucose levels to a Bluetooth radio, cellular phone or personal digital assistant (PDA).

EXAMPLE 40

In some embodiments of the present invention, a integrated blood glucose monitoring unit is employed that comprises a blood glucose test strip reader that is able to read accurately any of two or more commercial brands of blood glucose test strips, or comprises a blood glucose monitor that is capable of using digital output accurately from any of two or more commercial brands of blood glucose test strip readers. The blood glucose monitoring unit further comprises a calibration unit that is integrated with one or more components of a noninvasive glucose monitoring system to enable calibration of the noninvasive system based on in vitro data from the test strips.

The integrated blood glucose monitoring unit of this example comprises a glucose monitor for evaluation of invasively obtained blood samples, and further comprises a calibration unit to adjust the numerical translation of times of flight for electromagnetic wave signals or ultrasound in particular. The numerical translation converts times of flight from tissue dimensions (or changes in the dimensions) to corresponding blood glucose concentration levels. The tissue dimensions that are measured include but are not limited to: thickness, length, width, diameter, curvature, and roughness. In particular, embodiments the wave frequencies employed are for ultrasound or coherent optical pulses.

Blood glucose concentrations determined by blood sample on the test strips are used to validate or as necessary to adjust metrics in an algorithm for numerical translation from times of flight to blood glucose concentration level. This validation or adjustment serves as the means of calibration for the noninvasive monitor. The data from the invasive tests needs to be collected no more often than is commonly done for invasive-only tests. The frequency of such tests varies with the health and preferences of the individual subjects but in a typical range the time between tests is between 3 and 24 hours.

The foregoing description and drawings comprise illustrative embodiments of the preferred embodiment, but the invention is not so limited. It will be readily apparent to those of ordinary skill in the art that numerous alternatives, variations, modifications and permutations of the invention described herein may be made without departing from the spirit or nature of the invention; these are contemplated as being part of the invention. Also, merely listing or enumerating the steps of a method or the components of a device in a certain order does not constitute any limitation on the order of the steps or components of that method or device, respectively. Although specific terms are employed herein, they are used in descriptive sense only and not for purposes of limitation.

We claim:
1. An integrated blood glucose monitoring device comprising a single housing, containing therein the following components:
 a) a blood glucose monitor;
 b) a noninvasive detector for blood glucose, wherein said detector is in communication with the blood glucose monitor;
 c) a blood sampler that is in communication with the blood glucose monitor;
 d) a data storage module that is in communication with the blood glucose monitor;
 e) a detector for a non-physiological ancillary factor, wherein the factor is selected from the group consisting of time of day, passage of time, ambient external pressure, atmospheric pressure, atmospheric humidity, electronic signal-to-noise ratio, and electronic signal drift;
 f) an ancillary monitor that is in communication with the data storage module and the detector for a non-physiological ancillary factor; and
 g) a computing processor unit that is in communication with the data storage module;
wherein:
 i) the blood glucose monitor is capable of:
  A) using an input from the blood sampler as a benchmark to calibrate a value detected by the noninvasive detector for blood glucose;
  B) using an input from the data storage module to calibrate a value detected by the noninvasive detector for blood glucose; and
  C) storing in the data storage module data from the calibration;
 ii) the ancillary monitor is capable of:
  A) comparing between values detected by the detector for a non-physiological ancillary factor and values detected by the blood sampler; and
  B) storing in the data storage module data from the comparison; and
 iii) the computing processor unit is capable of calculating a prediction of evolution of blood glucose values by application of a parametric model to successive values that are stored in the data storage module, wherein the stored successive values are measured or calculated values obtained from at least one component selected from the group consisting of: blood sampler, noninvasive detector, blood glucose monitor, ancillary factor detector, and ancillary monitor.
2. The integrated device according to claim 1, further comprising a data access interface that is in communication with the data storage module.

3. The integrated device according to claim 1, further comprising an alarm circuit that is in communication with at least one of the blood glucose monitor, ancillary monitor and computing processor.

4. The integrated device according to claim 1, further comprising an alarm circuit that is in communication with the computing processor, wherein the integrated devices additionally comprises at least one module that is selected from the group consisting of a display and a status transmitter, and wherein that module is in communication with the alarm circuit.

5. The integrated device according to claim 4, wherein the module is a status transmitter that is further in communication with a status receiver.

6. The device according to claim 1, further comprising an ancillary factor detector for a physiological condition, wherein said detector is in communication with an ancillary monitor and said monitor is in communication with the data storage module.

7. A method for monitoring blood glucose, comprising using a device according to claim 1 to determine a concentration or rate of change for blood glucose levels according to the following steps:
   a) transmitting into the body of a subject an electromagnetic wave at an energy level below a level that would compromise the integrity of tissues;
   b) receiving from the subject's body an electromagnetic wave that was transmitted into the body at step (a), and detecting said received wave by means of the noninvasive detector of blood glucose;
   c) correlating data from said noninvasive detector with a relative level of blood glucose;
   d) receiving a sample of blood in the blood sampler;
   e) determining a glucose concentration of said blood sample by means of said sampler;
   f) storing a glucose concentration value from at least one of said detector and said sampler in the data storage module of claim 1;
   g) comparing and calibrating a glucose concentration value from said detector with a benchmark value from said sampler by means of the blood glucose monitor of claim 1;
   h) tracking an environmental condition by means of the non-physiological ancillary factor detector of claim 1;
   i) by means of the ancillary monitor of claim 1, comparing a signal value from said ancillary detector with another signal value from said ancillary detector and or with a signal value from said blood sampler;
   wherein steps a and d may be performed in any order relative to each other.

8. The method for monitoring blood glucose according to claim 7, further comprising in any order the step of transferring information to or from the blood glucose monitoring device by means of a data access interface that is in communication with the data storage module.

9. The method for monitoring blood glucose according to claim 7, further comprising the step of comparing blood glucose concentration values from the blood glucose monitor with a programmed boundary for health and safety, wherein the comparison is performed by means of an alarm circuit that is in communication with the blood glucose monitor.

10. The method for monitoring blood glucose according to claim 7, further comprising the step of issuing an alarm by means of an alarm circuit that is in communication with the blood glucose monitor and also in communication with at least one module that is a display or status transmitter, in the event that data for a blood glucose concentration or a blood glucose concentration rate change falls outside a programmed boundary for health and safety.

11. The method for monitoring blood glucose according to claim 7, further comprising the step of transmitting a signal by means of a status transmitter that is in communication with an alarm circuit that is respectively in communication with the blood glucose monitor, wherein the transmitted signal is received by a remote status receiver.

12. The method for monitoring blood glucose according to claim 7, further comprising the step of detecting one or more values for a physiological condition other than the concentration of glucose in the blood or the rate of change for blood glucose concentrations, wherein said other physiological condition is detected by means of an ancillary factor detector that is in communication with an ancillary monitor that is respectively in communication with the data storage module.

13. The method for monitoring blood glucose according to claim 7, further comprising displaying data on the blood glucose concentration and the environmental condition on a display that is in communication with an alarm circuit that is respectively in communication with the blood glucose monitor.

14. The method according to claim 7 wherein the transmitted and received wave is of a type that is detectable noninvasively by a sensor for a modality that is selected from the group consisting of: ultrasound, optical coherence tomography, infrared light, near-infrared light, thermal infrared spectroscopy, Raman spectroscopy, nuclear magnetic resonance, electron spin resonance, polarized light, electromagnetic waves, radiofrequency waves, impedance spectroscopy, dielectric spectroscopy, photoacoustic technology, beam-splitting optics, and reverse iontophoresis.

15. The method of claim 7 wherein the subject is selected from the group consisting of humans, pets, livestock, research animals and display animals.

* * * * *